US012745989B2

(12) United States Patent
Gu et al.

(10) Patent No.: US 12,745,989 B2
(45) Date of Patent: Sep. 29, 2026

(54) MEDICAL IMAGING METHOD, MEDICAL IMAGING SYSTEM, AND NON-TRANSITORY COMPUTER-READABLE MEDIUM

(71) Applicant: GE Precision Healthcare LLC, Waukesha, WI (US)

(72) Inventors: Minyu Gu, Wuxi (CN); Gang Liu, Wuxi (CN); Zhiwen Wang, Wuxi (CN); Weijie Zhang, Wuxi (CN); Ke Tao, Wuxi (CN); Feng Wu, Wuxi (CN)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 18/777,998

(22) Filed: Jul. 19, 2024

(65) Prior Publication Data

US 2025/0025134 A1 Jan. 23, 2025

(30) Foreign Application Priority Data

Jul. 20, 2023 (CN) ......................... 202310899096.9

(51) Int. Cl.
*A61B 8/00* (2006.01)
*G16H 40/67* (2018.01)

(52) U.S. Cl.
CPC .............. *A61B 8/54* (2013.01); *A61B 8/4236* (2013.01); *A61B 8/4477* (2013.01); *G16H 40/67* (2018.01)

(58) Field of Classification Search
CPC ....... A61B 8/54; A61B 8/4236; A61B 8/4477; A61B 8/4472; A61B 8/56; A61B 8/565; A61B 5/055; A61B 6/032; A61B 8/14; G16H 40/67; G16H 30/20
See application file for complete search history.

(56) References Cited

U.S. PATENT DOCUMENTS

2012/0109682 A1* 5/2012 Seltzer .................... G16Z 99/00 705/2
2013/0023753 A1* 1/2013 Kawamura .......... G01R 33/288 600/410
2022/0399107 A1* 12/2022 Shen ....................... G16H 40/20
2023/0404541 A1* 12/2023 Fiegoli .................... G10L 15/22
2024/0023909 A1* 1/2024 Xiang .................... A61B 6/032
2024/0115238 A1* 4/2024 Nally .................. A61B 8/0891

FOREIGN PATENT DOCUMENTS

CN 104107067 A 10/2014
CN 106377280 B 8/2018
WO 2013038217 A1 3/2013

* cited by examiner

*Primary Examiner* — Alexei Bykhovski

(57) ABSTRACT

A medical imaging method, a medical imaging system, and a non-transitory computer-readable medium. The medical imaging method includes: controlling at least two medical imaging devices to perform communication with each other; generating an imaging protocol for different sites to be imaged of the same subject to be imaged, the imaging protocol including an allocation of the different sites to be imaged in the at least two medical imaging devices; and sending the imaging protocol to each of the at least two medical imaging devices.

13 Claims, 5 Drawing Sheets

MEDICAL IMAGING METHOD, MEDICAL IMAGING SYSTEM, AND NON-TRANSITORY COMPUTER-READABLE MEDIUM

CROSS-REFERENCE TO RELATED APPLICATION

This application claim priority to Chinese Patent Application No. 202310899096.9, which was file on Jul. 20, 2023 at the Chinese Patent Office. The entire contents of the above-listed application are incorporated by reference herein in their entirety.

TECHNICAL FIELD

Embodiments of the present application relate to the technical field of medical devices, and relate in particular to a medical imaging method, a medical imaging system, and a non-transitory computer-readable medium.

BACKGROUND

Medical imaging devices are capable of non-invasively obtaining internal tissue images of a subject to be imaged. For example, a scanning device of the medical imaging device may scan a predetermined site of the subject to be imaged to obtain imaging data including information of the predetermined site.

Common medical imaging devices are, for example, ultrasound imaging systems, nuclear magnetic resonance imaging (MRI) systems, computed tomography (CT) scanning systems, etc.

It should be noted that the above introduction of the background is only for the convenience of clearly and completely describing the technical solutions of the present application, and for the convenience of understanding for those skilled in the art.

SUMMARY

In some cases, a plurality of sites of a subject to be imaged need to be scanned, and for different sites, the type of scanning device (for example, probe) may need to be adjusted, or parameters may need to be adjusted. A scanner, such as a doctor, typically needs to plan an appropriate scanning path and perform scans one by one. Such a scanning process is very time-consuming. In some scenarios, such as emergency scenarios, the problem of scanning inefficiency will be more prominent.

In order to solve at least one technical problem described above or similar technical problems, embodiments of the present application provide a medical imaging method, a medical imaging system, and a non-transitory computer-readable medium. In the medical imaging method, an imaging protocol is generated to comprise an allocation of different sites to be imaged for the same subject to be imaged in at least two medical imaging devices, and the imaging protocol is sent to the at least two medical imaging devices, so that the at least two medical imaging devices can operate in cooperation on the basis of the imaging protocol.

According to one aspect of the embodiments of the present application, a medical imaging method is provided. The method comprises:

controlling at least two medical imaging devices to perform communication with each other;

generating an imaging protocol for different sites to be imaged of the same subject to be imaged, the imaging protocol comprising an allocation of the different sites to be imaged in the at least two medical imaging devices; and sending the imaging protocol to each of the at least two medical imaging devices.

According to another aspect of the embodiments of the present application, a medical imaging system is provided. The medical imaging system comprises a first processor, wherein the first processor is configured to perform the medical imaging method as described in the above embodiments.

According to still another aspect of the embodiments of the present application, a non-transitory computer-readable medium is provided. The non-transitory computer-readable medium has a computer program stored therein, wherein the computer program has at least one code segment, and the at least one code segment is executable by a machine so as to cause the machine to perform the steps of the method as described in the above embodiments.

One of the beneficial effects of the examples of the present application is that: In the medical imaging method, an imaging protocol is generated to comprise an allocation of different sites to be imaged for the same subject to be imaged in at least two medical imaging devices, and the imaging protocol is sent to the at least two medical imaging devices, so that the at least two medical imaging devices can operate in cooperation on the basis of the imaging protocol.

With reference to the following description and drawings, specific embodiments of the examples of the present application are disclosed in detail, and the means by which the principles of the examples of the present application can be employed are illustrated. It should be understood that the embodiments of the present application are therefore not limited in scope. Within the scope of the spirit and clauses of the appended claims, the embodiments of the present application include many changes, modifications, and equivalents.

BRIEF DESCRIPTION OF THE DRAWINGS

The included drawings are used to provide further understanding of the examples of the present application, which constitute a part of the description and are used to illustrate the embodiments of the present application and explain the principles of the present application together with textual description. Evidently, the drawings in the following description are merely some examples of the present application, and a person of ordinary skill in the art may obtain other embodiments according to the drawings without involving inventive skill. In the drawings.

DETAILED DESCRIPTION

The foregoing and other features of the examples of the present application will become apparent from the following description and with reference to the drawings. In the description and drawings, specific embodiments of the present application are disclosed in detail, and part of the embodiments in which the principles of the examples of the present application may be employed are indicated. It should be understood that the present application is not limited to the described embodiments. On the contrary, the examples of the present application include all modifications, variations, and equivalents which fall within the scope of the appended claims.

In the examples of the present application, the terms "first" and "second" and so on are used to distinguish different elements from one another by their title, but do not represent the spatial arrangement, temporal order, or the like of the elements, and the elements should not be limited by said terms. The term "and/or" includes any one of and all combinations of one or more associated listed terms. The terms "comprise", "include", "have", etc., refer to the presence of stated features, elements, components, or assemblies, but do not exclude the presence or addition of one or more other features, elements, components, or assemblies. The terms "pixel" and "voxel" may be used interchangeably.

In the examples of the present application, the singular forms "a" and "the" or the like include plural forms, and should be broadly construed as "a type of" or "a kind of" rather than being limited to the meaning of "one". Furthermore, the term "the" should be construed as including both the singular and plural forms, unless otherwise specified in the context. In addition, the term "according to" should be construed as "at least in part according to . . . ", and the term "based on" should be construed as "at least in part based on . . . ", unless otherwise clearly specified in the context.

The features described and/or illustrated for one embodiment may be used in one or more other embodiments in an identical or similar manner, combined with features in other embodiments, or replace features in other embodiments. The term "include/comprise" when used herein refers to the presence of features, integrated components, steps, or assemblies, but does not exclude the presence or addition of one or more other features, integrated components, steps, or assemblies.

Some embodiments of the present application provide a medical imaging method.

Figure 1:
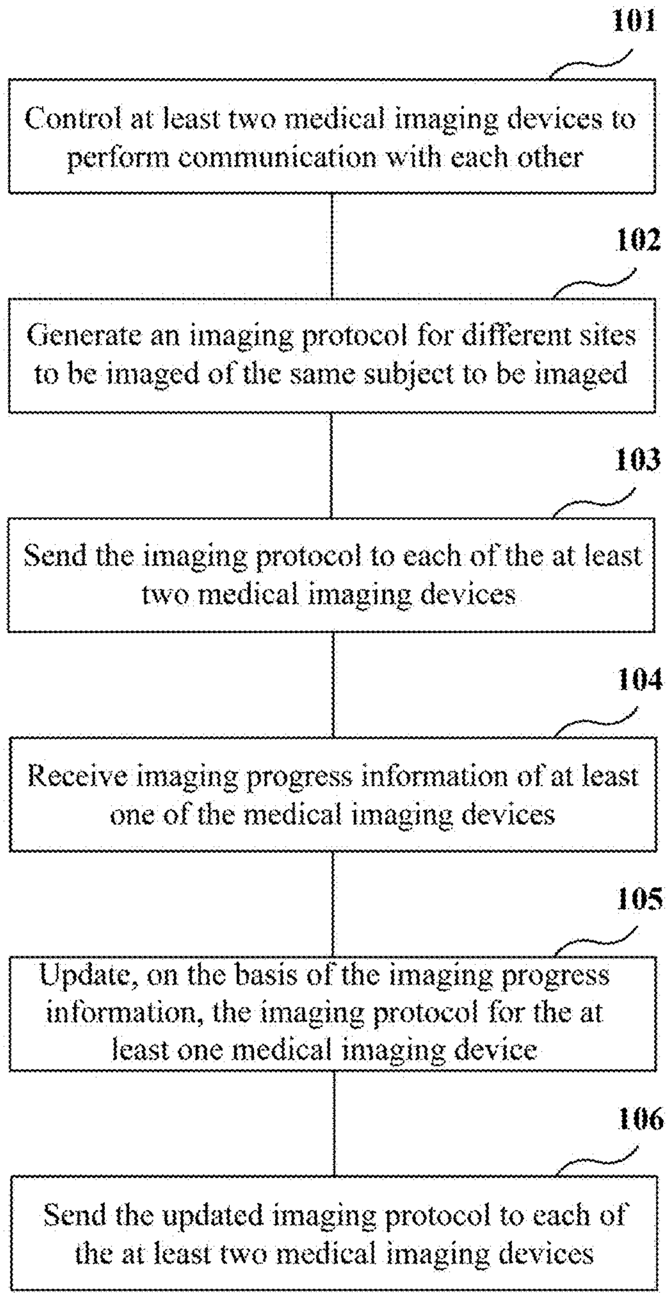
FIG. 1 is a schematic diagram of a medical imaging method according to some embodiments of the present application.

FIG. 1 is a schematic diagram of a medical imaging method according to some embodiments of the present application. As shown in FIG. 1, the medical imaging method includes:

operation 101, controlling at least two medical imaging devices to perform communication with each other;

operation 102, generating an imaging protocol for different sites to be imaged of the same subject to be imaged, the imaging protocol including an allocation of the different sites to be imaged in the at least two medical imaging devices; and operation 103, sending the imaging protocol to each of the at least two medical imaging devices.

In such a configuration manner, in one aspect, it can be ensured that the at least two medical imaging devices each perform their own imaging functions, and efficient data processing is ensured, and in another aspect, the shared imaging protocol can ensure that the respective medical imaging devices cooperate with each other and that optimization of a workflow is achieved.

In the present application, the imaging protocol may include: an allocation of different sites to be imaged in at least two medical imaging devices (i.e., the scanning order of different sites to be imaged of the same subject to be imaged by each medical imaging device), and/or information such as the degree of scanning completion of different sites to be imaged of the same subject to be imaged by each medical imaging device.

In at least one embodiment, the allocation of the different sites to be imaged in the at least two medical imaging devices may be, for example:

S1: using medical imaging device A to scan site a to be imaged, and using medical imaging device B to scan site b to be imaged;

S2: using, after completing the scanning of site a, medical imaging device A to scan site c to be imaged;

S3: using, after completing the scanning of site b, medical imaging device B to scan site d to be imaged;

In at least one embodiment, the degree of scanning completion may include imaging progress information and/or imaging result information, for example. The imaging progress information may include information such as whether scanning of a site to be imaged is completed. The imaging result information may include information such as whether the scanning result of the site to be imaged indicates that the site to be imaged is normal or abnormal. In addition, in a case where an operator saves a medical image, the imaging result information may further include the saved medical image.

According to the medical imaging method of the present application, the imaging protocol is sent to at least two medical imaging devices, and therefore, the at least two medical imaging devices can operate in cooperation on the basis of the imaging protocol. In particular, when a medical imaging device does not have a plurality of scanning devices, or the plurality of scanning devices of the medical imaging device cannot satisfy scanning for a plurality of sites to be imaged of the same subject to be imaged, on the basis of the medical imaging method according to the present application, at least two medical imaging devices can be enabled to operate in cooperation, thereby overcoming the limitations of a single medical imaging device to satisfy rapid scanning for the plurality of sites to be imaged of the subject to be imaged.

In at least one embodiment, each medical imaging device is, for example, an ultrasound imaging system, a nuclear magnetic resonance imaging (MRI) system, an electronic computed tomography (CT) scanning system, or the like. In the following description of the present application, an example will be described in which each medical imaging device is an ultrasound imaging system, but the content of these descriptions is not limited to the ultrasound imaging system and is also applicable to other types of medical imaging systems.

In the medical imaging device as the ultrasound imaging system, a scanning device includes, for example, a probe, and the scanning device is capable of emitting ultrasonic waves towards a site to be imaged of a subject to be imaged and receiving echoes of the ultrasonic waves, thereby obtaining imaging data. The imaging data may be used to generate a medical image, and the medical image currently scanned and acquired refers to a medical image (for example, an anatomical image of a particular slice, etc.) that may reflect the state (for example, morphology) at a current time (i.e., real-time) of an imaged site (for example, organs or tissues such as a blood vessel and the heart) of the subject to be imaged.

As described above in the present application, in a scenario in which scanning of different sites to be imaged of the same subject to be imaged using at least two medical imaging devices is required, the implementation of the embodiments of the present application for the cooperative operation of the at least two medical imaging devices will have a more significant effect. The present application will be described below in conjunction with a specific use scenario of medical imaging devices.

In the scenario of using an ultrasonic imaging device to perform focused assessment with sonography for trauma (FAST) or extended focused assessment with sonography for trauma (E-FAST), on the basis of the medical imaging method of the present application, operator (for example, a doctor) may use at least two medical imaging devices to scan different sites to be imaged of the same subject to be imaged, so that the limitations of the respective medical imaging devices can be overcome and scanning efficiency can be greatly improved.

Figure 2:
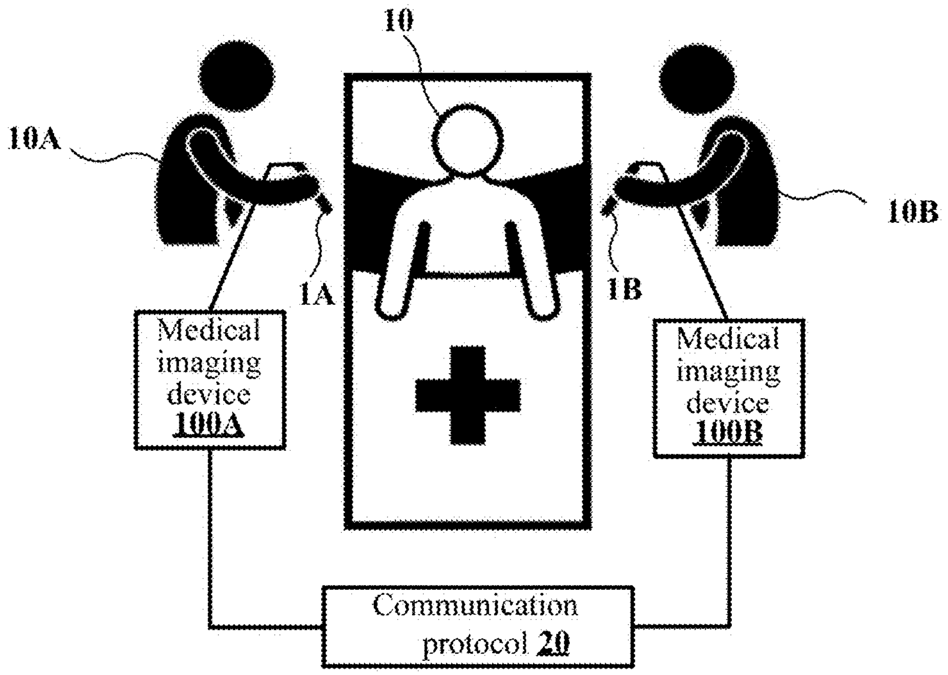
FIG. 2 is a schematic diagram of a use scenario according to the present application.

FIG. 2 is a schematic diagram of the scenario. As shown in FIG. 2, in this scenario, an operator 10A may use a scanning device 1A of a medical imaging device 100A to scan a subject to be imaged 10, and an operator 10B may use a scanning device 1B of a medical imaging device 100B to scan the subject to be imaged 10. The scanning device 1A and the scanning device 1B may be the same type of scanning device, or different types of scanning devices. In FIG. 2, only the case in which the number of operators is two and the number of medical imaging devices is two is shown, but the present application is not limited thereto, and the following description is also applicable to cases in which the number of operators is three or more and the number of medical imaging devices is three or more.

As shown in FIG. 2, the scanning device 1A and the scanning device 1B may simultaneously scan different sites to be imaged of the subject to be imaged 10, thereby improving the scanning efficiency for a plurality of sites of the subject to be imaged 10.

In an embodiment of the present application, the medical imaging method shown in FIG. 1 may be performed under the control of a first processor.

In at least one embodiment, the first processor may be disposed in at least one of the at least two imaging devices (for example, the imaging device 100A and the imaging device 100B). For example, a processor of one of the at least two imaging devices may be used as the first processor, or some functions of the first processor may be completed by a processor of one of the at least two imaging devices, and some other functions of the first processor may be completed by a processor of the other of the at least two imaging devices.

In at least one other embodiment, the first processor may be disposed outside the at least two imaging devices (for example, the imaging device 100A and the imaging device 100B). For example, the first processor may be disposed in a cloud server to communicate with the at least two imaging devices by means of a wired or wireless network.

In an embodiment of the present application, at least one of the at least two imaging devices may be set as a master device. The master device may be used to process images, and/or receive information sent by other imaging devices, and/or control other imaging devices, etc.

Figure 3:
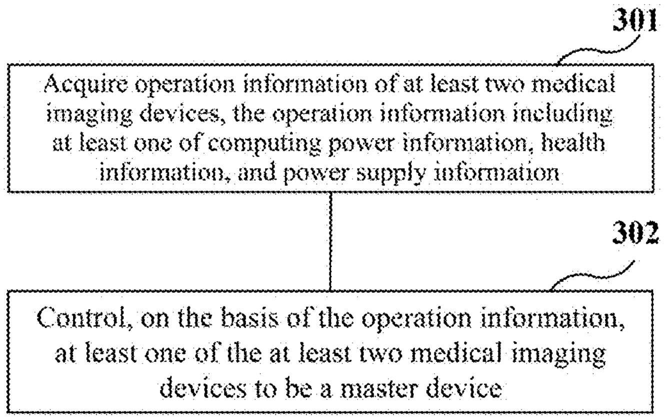
FIG. 3 is a schematic diagram of a method for setting a master device.

FIG. 3 is a schematic diagram of a method for setting a master device. As shown in FIG. 3, the method includes:

operation 301, acquiring operation information of at least two medical imaging devices, the operation information including at least one of computing power information, health information, and power supply information; and operation 302, controlling, on the basis of the operation information, at least one of the at least two medical imaging devices to be a master device.

For example, the first processor may communicate with each medical imaging device among the at least two medical imaging devices, thereby obtaining the operation information (for example, the operation information may be at least one of computing power information, health information, and power supply information) of each medical imaging device. Then, the first processor selects, as the master device, the medical imaging device having the highest computing power, and/or the highest degree of health, and/or the most stable power supply (or the most power remaining in the battery) on the basis of the operation information.

For another example, when the at least two medical imaging devices can communicate in a wired or wireless manner, their own operation information is thereby sent to other medical imaging devices, and operation information (for example, the operation information may be at least one of computing power information, health information, and power supply information) of the other medical imaging devices is received. Then, comparison and communication are performed using a rule (for example, an election rule or the like) preset in each medical imaging device, thereby determining a medical imaging device serving as the master device.

In addition, the present application is not limited thereto, and the master device may also be set by other methods. For example, at least one medical imaging device is manually set as a master imaging device by an operator, or a certain priority is set for each medical imaging device, and the master device is set on the basis of the priority (for example, when a medical imaging device having a high priority and a medical imaging device having a low priority are included in the at least two medical imaging devices, the medical imaging device having the high priority is automatically set as the master device).

In the present application, as shown in FIG. 2, the at least two imaging devices (for example, the imaging device 100A and the imaging device 100B) may perform communication on the basis of a certain communication protocol 20.

In at least one embodiment, the first processor may control the medical imaging devices (for example, the imaging device 100A and the imaging device 100B) to perform communication with each other on the basis of a predetermined communication protocol. Alternatively, the first processor may select a communication protocol from among at least two communication protocols for the medical imaging devices for example, the imaging device 100A and the imaging device 100B) to perform communication with each other.

For example, when the at least two imaging devices (for example, the imaging device 100A and the imaging device 100B) are started or under other conditions, each medical imaging device may independently communicate with the first processor using a communication protocol and inform the first processor of which communication protocols the medical imaging device is configured with. The first processor may select a common communication protocol with which each medical imaging device is configured, and notify each medical imaging device of the selection result. Each medical imaging device calls the common communication protocol according to the selection result sent by the first processor, and performs communication setting between the medical imaging devices on the basis of the common communication protocol. Thus, the respective medical imaging devices can perform communication with each other on the basis of the common communication protocol, so that information can be sent in a form such as broadcasting.

For another example, when the at least two medical imaging devices (for example, the imaging device 100A and the imaging device 100B) are started or under other conditions, each medical imaging device may independently communicate with the first processor using a communication protocol and inform the first processor of which communication protocols the medical imaging device is configured with. If the respective medical imaging devices are not configured with a common communication protocol, the first processor may configure a common communication protocol for the respective medical imaging devices, thereby enabling communication between the respective medical imaging devices on the basis of the common communication protocol. Alternatively, if the respective medical imaging devices are not configured with a common communication protocol, the controller may receive information from the respective medical imaging devices and forward the received information to other medical imaging devices, thereby implementing indirect communication between the medical imaging devices.

In the present application, communication is directly performed between at least two medical imaging devices (for example, the imaging device 100A and the imaging device 100B), and thus imaging progress information and/or imaging result information of each of the medical imaging devices may be sent to other medical imaging devices. Therefore, each medical imaging device can obtain not only its own imaging progress information and/or imaging result information, but also imaging progress information and/or imaging result information of other medical imaging devices. Thus, each medical imaging device may display, on its own display, or print, by means of a printer, the imaging progress information and/or imaging result information of the medical imaging device itself, and each medical imaging device may display, on its own display, or print, by means of a printer, the imaging progress information and/or imaging result information of the other medical imaging devices.

In addition, the present application is not limited thereto, and the at least two medical imaging devices (for example, the imaging device 100A and the imaging device 100B) may also send respective imaging progress information and/or imaging result information to the controller, and the controller may send the imaging progress information and/or the imaging result information as an imaging protocol to other medical imaging devices. Thus, each medical imaging device obtains imaging progress information and/or imaging result information of other medical imaging devices, thereby performing display or printing.

How the first processor sets the allocation of different sites to be imaged in the at least two medical imaging devices (i.e., the scanning order of different sites to be imaged of the same subject to be imaged by each medical imaging device) will be described below.

When the at least two medical imaging devices are started, the first processor generates an imaging protocol for different sites to be imaged of the same subject to be imaged, the imaging protocol including information of the allocation of the different sites to be imaged in the at least two medical imaging devices.

The imaging protocol may be an initial imaging protocol. For example, the first processor may generate the initial imaging protocol by setting the allocation of different sites to be imaged in at least two medical imaging devices according to probe characteristics of each medical imaging device, or according to a default scanning order. The initial imaging protocol is sent to the at least two medical imaging devices (for example, the imaging device 100A and the imaging device 100B), and thus, each medical imaging device may operate according to the imaging protocol. For example, each medical imaging device may display on its own display information of a current site to be imaged by the medical imaging device. In addition, the display of each medical imaging device may further display information of current sites to be imaged by other medical imaging devices.

In at least one embodiment, the allocation of different sites to be imaged in the at least two medical imaging devices in the initial imaging protocol may be, for example:

S1: using the medical imaging device 100A to scan site a to be imaged while using the medical imaging device 100B to scan site b to be imaged;

S2: using, after completing the scanning of site a, the medical imaging device 100A to scan site c to be imaged;

S3: using, after completing the scanning of site b, the medical imaging device 100B to scan site d to be imaged;

S4: using, after completing the scanning of site c, the medical imaging device 100A to scan site e to be imaged;

S5: using, after completing the scanning of site d, the medical imaging device 100B to scan site f to be imaged;

During the imaging process performed by each medical imaging device (for example, the imaging device 100A or the imaging device 100B), the first processor may perform the following operations as shown in FIG. 1:

operation 104, receiving imaging progress information of at least one of the medical imaging devices;

operation 105, updating, on the basis of the imaging progress information, the imaging protocol for the at least one medical imaging device; and operation 106, sending the updated imaging protocol to each of the at least two medical imaging devices.

Here, in operation 104, each medical imaging device (for example, the imaging device 100A or the imaging device 100B) may send imaging progress information to the first processor after completing imaging of a current site to be imaged.

In operation 105, the first processor, in the case of receiving the imaging progress information, may determine whether imaging (i.e., scanning) of the current site to be imaged by the medical imaging device is completed, and if it is completed, update the imaging protocol. The allocation of different sites to be imaged in the at least two medical imaging devices in the imaging protocol may be updated.

For example, if the scanning time for site a is long and the scanning time for site b is short, then after the scanning of site b is completed, the allocation of the imaging sites in the at least two medical imaging devices is updated to the following form:

S1: using the medical imaging device 100A to scan site a to be imaged while using the medical imaging device 100B to scan site d to be imaged;

S2: using, after completing the scanning of site a, the medical imaging device 100A to scan site c to be imaged;

S3: using, after completing the scanning of site d, the medical imaging device 100B to scan site f to be imaged;

S4: using, after completing the scanning of site c, the medical imaging device 100A to scan site e to be imaged;

For another example, if the scanning time for site a is long and the scanning time for site b is short, and site c may also be scanned using the scanning device 10B of the imaging device 100B, then after the scanning of site b is completed, the allocation of the imaging sites in the at least two medical imaging devices is updated to the following form:

S1: using the medical imaging device 100A to scan site a to be imaged while using the medical imaging device 100B to scan site c to be imaged;

S2: using, after completing the scanning of site a, the medical imaging device 100A to scan site e to be imaged;

S3: using, after completing the scanning of site c, the medical imaging device 100B to scan site d to be imaged;

In addition, in operation 105, the updated imaging protocol may further include the imaging progress information and/or imaging result information sent by each medical imaging device (for example, the imaging device 100A or the imaging device 100B) to the first processor.

In operation 106, the first processor may send the updated imaging protocol to each of the at least two medical imaging devices (for example, the imaging device 100A and the imaging device 100B). The updated imaging protocol includes an updated allocation of imaging sites in the at least two medical imaging devices, and the updated imaging protocol may further include the imaging progress information and/or imaging result information sent by each medical imaging device (for example, the imaging device 100A or the imaging device 100B) to the first processor.

In the present application, in a case where each of the at least two medical imaging devices (for example, the imaging device 100A and the imaging device 100B) receives the updated imaging protocol, each medical imaging device performs scanning according to the allocation (i.e., a scanning order) of imaging sites in the at least two medical imaging devices in the updated imaging protocol, and information of a current site to be imaged which is allocated to the medical imaging device is displayed on the display of the medical imaging device. In addition, each medical imaging device may also display imaging progress information and/or imaging result information of other medical imaging devices according to the imaging progress information and/or imaging result information in the updated imaging protocol.

Figure 4:
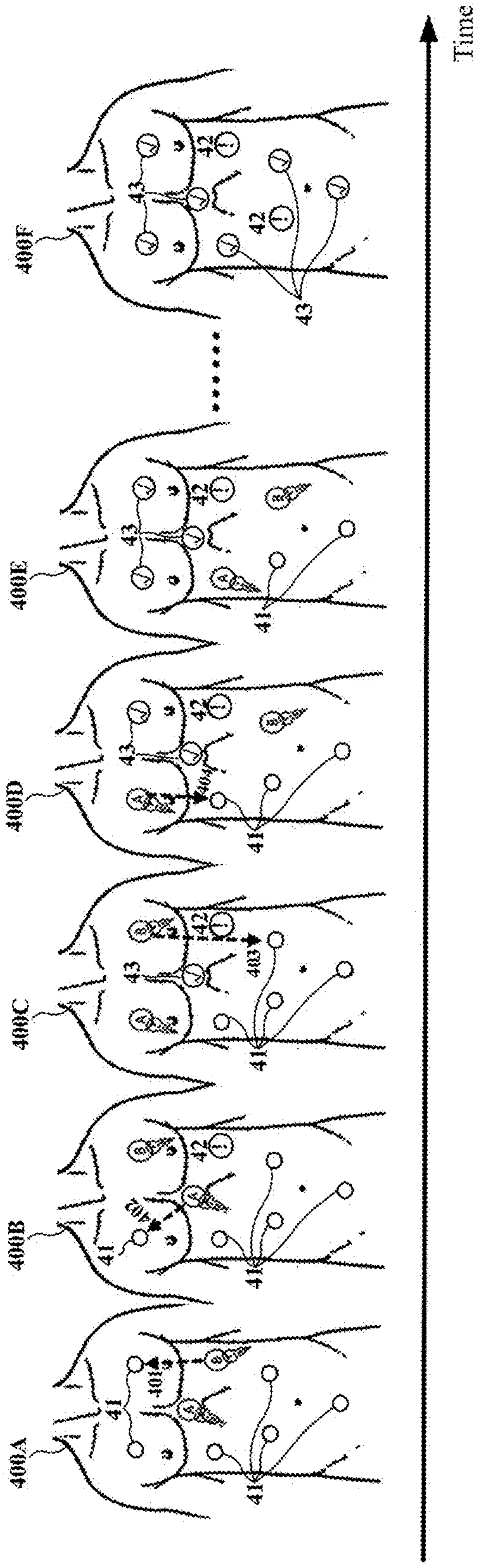
FIG. 4 is a schematic diagram of a screen displayed in a medical imaging device.

FIG. 4 is a schematic diagram of a screen displayed in the medical imaging device. For example, the schematic diagram of FIG. 4 may be a screen displayed by a display of the imaging device 100A or a display of the imaging device 100B.

As shown in FIG. 4, at time T1, a site to be imaged A which is currently imaged by the scanning device 10A and a site to be imaged B which is currently imaged by the scanning device 10B are shown in the screen 400A, in which icon A and icon B may be highlighted to emphasize the sites to be imaged which are currently imaged. For example, icon A and icon B may be displayed. In the screen 400A, an arrow 401 points to a next site to be imaged by the scanning device 10B, and icons 41 indicate sites to be imaged of the subject to be imaged which have not yet been imaged.

As shown in FIG. 4, at time T2, the screen is switched to 400B, in which an arrow 402 points to a next site to be imaged by the scanning device 10A, a site to be imaged which is currently imaged by the scanning device 10B is B, and an icon 42 is used to indicate first imaging result information of an imaged site. For example, the first imaging result information indicates that the imaging result for the imaged site is “abnormal”. The icons 41 indicate sites to be imaged of the subject to be imaged that have not yet been imaged.

As shown in FIG. 4, at time T3, the screen is switched to 400C, in which an arrow 403 points to a next site to be imaged by the scanning device 10B, a site to be imaged which is currently imaged by the scanning device 10A is A, and an icon 43 is used to indicate second imaging result information of an imaged site. For example, the second imaging result information indicates that the imaging result for the imaged site is “normal”. The icons 41 indicate sites to be imaged of the subject to be imaged that have not yet been imaged.

As shown in FIG. 4, at time T4, the screen is switched to 400D, in which an arrow 404 points to a next site to be imaged by the scanning device 10A, a site to be imaged which is currently imaged by the scanning device 10B is A, the icons 41 indicate sites to be imaged of the subject to be imaged that have not yet been imaged, the icon 42 is used to indicate the first imaging result information of the imaged site, and the icons 43 are used to indicate the second imaging result information of the imaged sites.

As shown in FIG. 4, at time T5, the screen is switched to 400E, in which an arrow 405 points to a next site to be imaged by the scanning device 10B, a site to be imaged which is currently imaged by the scanning device 10A is A, the icons 41 indicate sites to be imaged of the subject to be imaged that have not yet been imaged, the icon 42 is used to indicate the first imaging result information of the imaged site, and the icons 43 are used to indicate the second imaging result information of the imaged sites.

In FIG. 4, the icon 41 is a solid circle, the icon 42 is a combination of a circle and an exclamation point, and the icon 43 is a combination of a circle and a check mark. The present application may not be limited thereto as long as the icons 41, 42, and 43 can be visually distinguished from each other. For example, the icons 41, 42, and 43 may be different in at least one aspect such as display shape, display color, and flashing frequency.

After imaging for all sites to be imaged of the subject to be imaged is completed, a screen 400F as shown in FIG. 4 may be generated, and the screen 400F may indicate imaging result information of all of the sites to be imaged of the subject to be imaged. Since each medical imaging device sends the imaging progress information and the imaging result information to the other medical imaging devices, and each medical imaging device receives the imaging progress information and the imaging result information of the other medical imaging devices, each medical imaging device can obtain the information of the screen 400F so that the imaging result information of all of the sites to be imaged of the subject to be imaged is displayed on the respective displays or printed using a printer.

In addition, in an embodiment of the present application, when using a scanning device (for example, the scanning device 10A or 10B) to image a site to be imaged, an operator may operate a first button (for example, press the first button) of the scanning device, thereby generating imaging progress information indicating that imaging for a current site to be imaged is completed. In addition, the operator may also operate a second button of the scanning device, thereby generating imaging result information. For example, a single press of the second button by the operator indicates that the imaging result of the site to be imaged is "normal". Pressing, by the operator, the second button two or more times within a predetermined period of time indicates that the imaging result of the site to be imaged is "abnormal", and the medical imaging device may be caused to save a medical image of the site to be imaged as a part of the imaging result information. Thus, each medical imaging device may obtain the medical image saved by the medical imaging device and the medical images saved by the other medical imaging devices to be displayed on the respective displays or printed using a printer.

Some embodiments of the present application further provide a medical imaging system.

Figure 5:
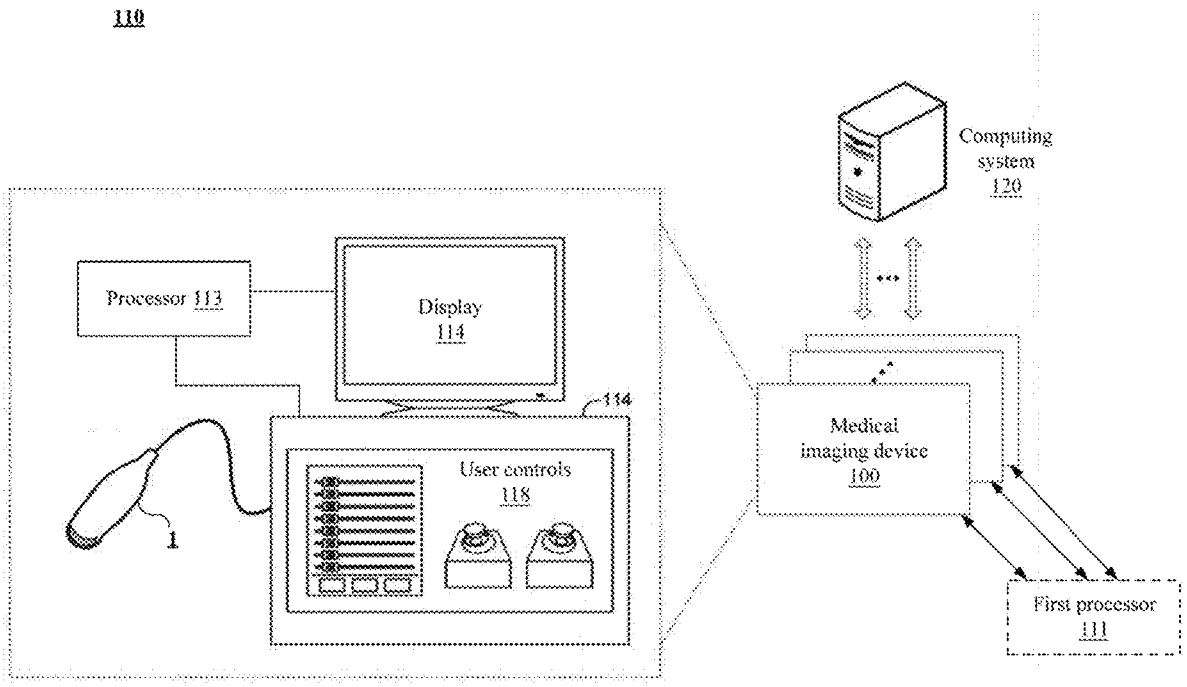
FIG. 5 is a schematic diagram of a medical imaging system according to an embodiment of the present application.

FIG. 5 is a schematic diagram of a medical imaging system according to an embodiment of the present application.

The medical imaging system 110 as shown in FIG. 5 may include a first processor 111. The first processor 111 is capable of controlling at least two medical imaging devices 100, thereby implementing the medical imaging method as described in any of the above embodiments. In some embodiments, the medical imaging system 110 may be independent from the medical imaging devices 100. It may be connected to the medical imaging devices 100 in a wired or wireless manner, and perform the method of any of the above embodiments of the present application by means of the first processor 111 therein to control imaging.

In some other embodiments, the medical imaging system 110 may also include the medical imaging devices 100. The medical imaging devices 100 are, for example, the medical imaging device 100A or 100B shown in FIG. 2. With reference to FIG. 5, the medical imaging devices 100 will be described below, and the description is applicable, for example, to the medical imaging devices 100A and 100B shown in FIG. 2.

As shown in FIG. 5, each medical imaging device 100 includes suitable hardware, software, or a combination thereof for supporting medical imaging (i.e., enabling data for generating and/or rendering images during a medical imaging examination to be obtained). For example, the medical imaging device 100 may be an ultrasound system or magnetic resonance system configured to be used to generate and/or render ultrasound images, etc.

As shown in FIG. 5, each medical imaging device 100 may include a scanning device 1, a display 114, and a processor 113, and the scanning device may be portable and movable.

In at least one embodiment of the present application, the first processor 111 may be disposed in at least one of the at least two imaging devices 100. For example, the processor 113 of one of the at least two imaging devices 100 is used as the first processor 111. In this case, the one of the at least two imaging devices 100 may be regarded as a medical imaging system 110. Alternatively, part of the functions of the first processor 111 may be completed by the processor 113 of one of the at least two imaging devices, and another part of the functions of the first processor 111 may be completed by the processor 113 of the other of the at least two imaging devices. In this case, the at least two imaging devices as a whole may be regarded as a medical imaging system 110.

Each scanning device 1 may be configured to be used to generate and/or capture specific types of imaging signals (and/or data corresponding thereto), for example, by means of moving above a subject to be imaged (or a part thereof), and may include suitable circuitry for performing and/or supporting such functions. The scanning device 1 may be an ultrasound probe, an MRI scanner, a CT scanner, or any suitable imaging device. In a case where the medical imaging device 100 is an ultrasound system, the scanning device 1 may emit an ultrasound signal and capture an echo ultrasound image. For example, the scanning device 1 may be a patch probe. For a description of the patch probe, for example, reference may be made to the patent document having the publication number CN 109419530 A, etc.

In the present application, each medical imaging device 100 as shown in FIG. 5 includes suitable hardware, software, or a combination thereof for supporting medical imaging (i.e., enabling data for generating and/or rendering images during a medical imaging examination to be obtained). For example, the medical imaging device 100 may be an ultrasound imaging system or magnetic resonance system configured to be used to generate and/or render ultrasound images, etc.

The display 114 may be configured to display images (e.g., via a screen). In some cases, the display 114 may also be configured to at least partially generate the displayed image. In addition, the display 114 may further support user input/output. For example, in addition to images, the display 114 may further provide (e.g., via the screen) user feedback (e.g., information related to the system, the functions and settings thereof, etc.). The display 114 may further support user input (e.g., via user controls 118) to, for example, allow control of medical imaging. User input can involve controlling the display of images, selecting settings, specifying user preferences, requesting feedback, etc. The display 114 may receive a signal from a processor and display it.

For example, the display 114 may display the screens 400A to 400F as shown in FIG. 4. Thus, an operator of each medical imaging device 100 can understand the imaging progress information and/or the imaging result information of the medical imaging device and other medical imaging devices by means of the screens, thereby facilitating the cooperative operation with the plurality of medical imaging devices to improve scanning efficiency.

In some embodiments, each medical imaging device 100 may further incorporate additional and dedicated computing resources, such as one or more computing systems 120. In this regard, each computing system 120 may include circuits, interfaces, logic, and/or code suitable for processing, storing, and/or communicating data. The computing system 120 may be a specialized device configured for use specifically in conjunction with medical imaging, or it may be a general-purpose computing system (e.g., a personal computer, server, etc.) that is set up and/or configured to perform the operations described below with respect to the computing system 120. The computing system 120 may be configured to support the operation of the medical imaging device 100, as described below. In this regard, various functions and/or operations can be offloaded from the imaging system, which may simplify and/or centralize certain aspects of processing to reduce costs (by eliminating the need to add processing resources to the imaging system).

The computing system 120 may be set up and/or arranged for use in different ways. For example, in some specific implementations, a single computing system 120 may be used; and in other specific implementations, a plurality of computing systems 120 are configured to work together (for example, configured on the basis of distributed processing), or individually. Each of the computing systems 120 is configured to process a specific aspect and/or function, and/or to process data only for a specific medical imaging device 100.

In some embodiments, the computing system 120 may be local (for example, co-located with one or a plurality of medical imaging devices 100, such as within the same facility and/or the same local network); and in other specific embodiments, the computing system 120 may be remote, and thus accessible only by means of a remote connection (for example, by means of the Internet or other available remote access technologies). In particular specific implementations, the computing system 120 may be configured in a cloud-based manner and may be accessed and/or used in a substantially similar manner to accessing and using other cloud-based systems.

Once data is generated and/or configured in the computing system 120, the data can be copied and/or loaded into the medical imaging device 100. This can be done in different ways. For example, the data may be loaded via a directed connection or link between the medical imaging device 100 and the computing system 120. In this regard, communication between the different components of the setup can be performed using available wired and/or wireless connections and/or according to any suitable communication (and/or networking) standards or protocols. Optionally or additionally, the data may be indirectly loaded into the medical imaging device 100. For example, the data may be stored in a suitable machine-readable medium (for example, a flash memory card or the like) and then loaded into the medical imaging device 100 (on-site, for example, by a user (such as an imaging clinician) of the system or authorized personnel) by using the machine-readable medium. Alternatively, the data may be downloaded to a locally communicative electronic device (for example, a laptop or the like) and then the electronic device is used (for example, by a user of the system or authorized personnel) on-site to upload the data to the medical imaging device 100 by means of a direct connection (for example, a USB connector or the like).

In operation, the medical imaging device 100 may be used to generate and present (for example, render or display) images during a medical examination and/or used in conjunction therewith to support user input/output. The images can be 2D, 3D, and/or 4D images. The particular operations or functions performed in the medical imaging device 100 to facilitate the generation and/or presentation of images depend on the type of system (i.e., the means used to obtain and/or generate the data corresponding to the images). For example, in ultrasound imaging, the data is based on the emitted ultrasound signal and the echo ultrasound signal.

Figure 6:
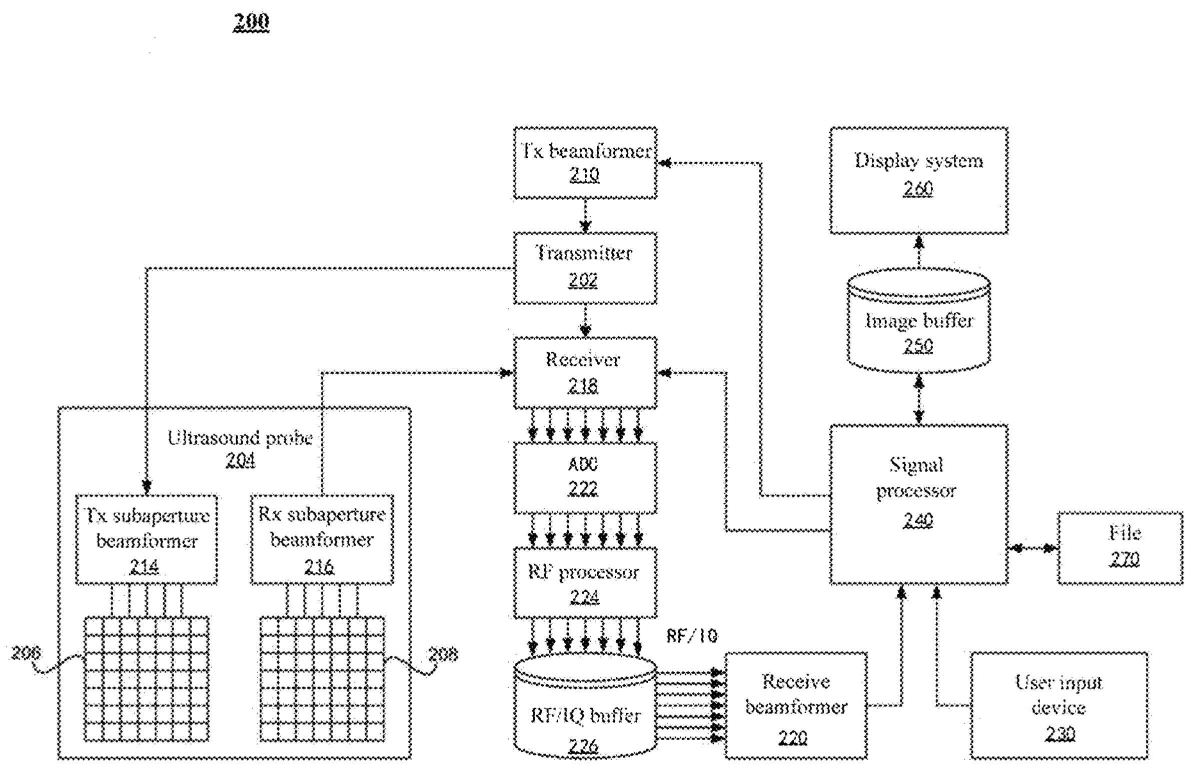
FIG. 6 is a schematic diagram of an ultrasound imaging system according to an embodiment of the present application.

FIG. 6 is a schematic diagram of an ultrasound imaging system according to an embodiment of the present application. As shown in FIG. 6, the ultrasound imaging system 200 may be configured to be used to provide ultrasound imaging, and may therefore include suitable circuitry, interfaces, logic, and/or code for performing and/or supporting ultrasound imaging related functions. The ultrasound imaging system 200 may correspond to the medical imaging device 100 of FIG. 5 or the medical imaging system 110.

The ultrasound imaging system 200 includes, for example, a transmitter 202, an ultrasound probe 204 (corresponding to the foregoing scanning device 1), a transmit beamformer 210, a receiver 218, a receive beamformer 220, an RF processor 224, an RF/IQ buffer 226, a user input module 230, a signal processor 240 (corresponding to the foregoing processor 114), an image buffer 250, a display system 260 (a display), and a file 270.

The transmitter 202 may include suitable circuitry, interfaces, logic, and/or code operable to drive the ultrasound probe 204. The ultrasound probe 204 may include an array of two-dimensional (2D) piezoelectric elements. The ultrasound probe 204 may include a set of transmitting transducer elements 206 and a set of receiving transducer elements 208 that typically form the same element. In some embodiments, the ultrasound probe 204 may be operable to acquire ultrasound image data covering at least a substantial portion of an anatomical structure (such as the heart or any suitable anatomical structure).

The transmit beamformer 210 may include suitable circuitry, interfaces, logic, and/or code that is operable to control the transmitter 202, and the transmitter 202 drives the set of transmitting transducer elements 206 through a transmitting subaperture beamformer 214 to transmit ultrasound emission signals into a region of interest (e.g., a person, animal, subsurface cavity, physical structure, etc.). The emitted ultrasound signal can be backscattered from structures in the subject of interest (e.g., blood cells or tissue) to produce echo. The echo is received by the receiving transducer elements 208.

The set of receiving transducer elements 208 in the ultrasonic probe 204 may be operated to convert the received echo to an analog signal for subaperture beam formation through a receiving subaperture beamformer 216, which is then transmitted to the receiver 218. The receiver 218 may include suitable circuitry, interfaces, logic, and/or code that is operable to receive signals from the receiving subaperture beamformer 216. The analog signal can be transferred to one or more of a plurality of A/D converters 222.

The plurality of A/D converters 222 may include suitable circuitry, interfaces, logic, and/or code that is operable to convert the analog signal from the receiver 218 to a corresponding digital signal. The plurality of A/D converters 222 are provided between the receiver 218 and the RF processor 224. Nevertheless, the present application is not limited in this regard. Thus, in some embodiments, the plurality of A/D converters 222 may be integrated within the receiver 218.

The RF processor 224 may include suitable circuitry, interfaces, logic, and/or code that is operable to demodulate the digital signals output by the plurality of A/D converters 222. According to one embodiment, the RF processor 224 may include a complex demodulator (not shown) that is operable to demodulate the digital signal to form an I/Q data pair representing the corresponding echo signal. The RF or I/Q signal data can then be transferred to the RF/IQ buffer 226. The RF/IQ buffer 226 may include suitable circuitry, interfaces, logic, and/or code that is operable to provide temporary storage of RF or I/Q signal data generated by the RF processor 224.

The receive beamformer 220 may include suitable circuitry, interfaces, logic, and/or code that may be operable to perform digital beamforming processing to, for example, sum and output a beam summing signal for the delay-channel signals received from the RF processor 224 via the RF/IQ buffer 226. The resulting processed information may be the beam summing signal outputted from the receive beamformer 220 and transmitted to the signal processor 240. According to some embodiments, the receiver 218, the plurality of A/D converters 222, the RF processor 224, and the beamformer 220 may be integrated into a single beamformer which may be digital. In various embodiments, the ultrasound imaging system 200 includes a plurality of receive beamformers 220.

The user input device 230 can be used to enter patient data, scan parameters, and settings, and select protocols and/or templates to interact with the AI segmentation processor, so as to select tracking targets, etc. In an illustrative embodiment, the user input device 230 is operable to configure, manage, and/or control the operation of one or more components and/or modules in the ultrasound imaging system 200. In this regard, the user input device 230 is operable to configure, manage, and/or control the operation of the transmitter 202, the ultrasound probe 204, the transmit beamformer 210, the receiver 218, the receive beamformer 220, the RF processor 224, the RF/IQ buffer 226, the user input device 230, the signal processor 240, the image buffer 250, the display system 260, and/or the file 270.

For example, the user input devices 230 may include buttons, rotary encoders, touch screens, motion tracking, voice recognition, mouse devices, keyboards, trackballs, cameras, and/or any other devices capable of receiving user commands. In some embodiments, for example, one or more of the user input devices 230 may be integrated into other components (such as the display system 260 or the ultrasound probe 204). As an example, the user input device 230 may include a touch screen display. As another example, the user input device 230 may include an accelerometer, gyroscope, and/or magnetometer attached to and/or integrated with the probe 204 to provide pose and motion recognition of the probe 204, such as identifying one or more probe compressions against the patient's body, predefined probe movements, or tilt operations, etc. Additionally and/or alternatively, the user input device 230 may include image analysis processing to identify the probe pose by analyzing the captured image data.

The signal processor 240 may include suitable circuitry, interfaces, logic, and/or code that is operable to process the ultrasound scan data (i.e., the summed IQ signal) to generate an ultrasound image for presentation on the display system 260. The signal processor 240 is operable to perform one or more processing operations based on a plurality of selectable ultrasound modalities on the acquired ultrasound scan data. In an illustrative embodiment, the signal processor 240 is operable to perform display processing and/or control processing, etc. As the echo signal is received, the acquired ultrasound scan data can be processed in real-time during the scan session. Additionally or alternatively, the ultrasound scan data may be temporarily stored in the RF/IQ buffer 226 during the scan session and processed in a less real-time manner during online or offline operation. In various embodiments, the processed image data may be presented at the display system 260 and/or may be stored in the file 270. The file 270 can be a local file, a picture archiving and communication system (PACS), or any suitable device for storing images and related information.

The signal processor 240 may be one or more central processing units, microprocessors, microcontrollers, etc. For example, the signal processor 240 may be an integrated component, or may be distributed in various locations. The signal processor 240 may be configured to receive input information from the user input device 230 and/or file 270, generate outputs that may be shown by the display system 260, and manipulate the outputs, etc., in response to the input information from the user input device 230. The signal processor 240 may be capable of executing, for example, any of one or more of the methods and/or one or more sets of instructions discussed herein according to various embodiments.

The ultrasound imaging system 200 may be operated to continuously acquire ultrasound scan data at a frame rate suitable for the imaging situation under consideration. Typical frame rates are in the range of 20 to 220, but can be lower or higher. The acquired ultrasound scan data can be shown on the display system 260 in real-time at a display rate that is the same as the frame rate, or slower, or faster than the frame rate. The image buffer 250 is included to store frames for processing of the acquired ultrasound scan data that are not scheduled for immediate display. Preferably, the image buffer 250 has sufficient capacity to store frames of ultrasound scan data for at least a few minutes. Frames of ultrasound scan data are stored in such a way that they can be easily retrieved therefrom according to their acquisition sequence or time. The image buffer 250 may be embodied in any known data storage medium.

In some specific embodiments, the signal processor 240 may be configured to perform or otherwise control at least some of the functions performed thereby based on user instructions via the user input device 230. As an example, the user may provide voice commands, probe poses, button presses, etc. to issue specific commands such as controlling aspects of automatic strain measurement and strain ratio calculations, and/or provide or otherwise specify various parameters or settings associated therewith, as described in more detail below.

In operation, the ultrasound imaging system 200 may be used to generate ultrasound images, including two-dimensional (2D), three-dimensional (3D), and/or four-dimensional (4D) images. In this regard, the ultrasound imaging system 200 may be operated to continuously acquire ultrasound scan data at a specific frame rate, which may be applicable to the imaging situation discussed. For example, the frame rate can be in the range of 20-70, or can be lower or higher. The acquired ultrasound scan data can be shown on the display system 260 at the same display rate as the frame rate, or slower, or faster than the frame rate. The image buffer 250 is included to store frames for processing of the acquired ultrasound scan data that are not scheduled for immediate display. Preferably, the image buffer 250 has sufficient capacity to store at least a few seconds of frames of ultrasound scan data. Frames of ultrasound scan data are stored in such a way that they can be easily retrieved therefrom according to their acquisition sequence or time. The image buffer 250 may be embodied in any known data storage medium.

In some cases, the ultrasound imaging system 200 may be configured to support grayscale and color-based operations. For example, the signal processor 240 may operate to perform grayscale B-model processing and/or color processing. Grayscale B-model processing may include processing B-model RF signal data or IQ data pairs. For example, the grayscale B-model processing can enable the formation of an envelope of the received beam summing signal by computing the amount $(I^2+Q^2)^{1/2}$. The envelope can be subjected to additional B-model processing, such as logarithmic compression to form the display data. The display data can be converted to X-Y format for video display. Scan-converted frames can be mapped to grayscale for display. The B-model frame is provided to the image buffer 250 and/or the display system 260. Color processing may include processing color-based RF signal data or IQ data pairs to form frames to cover the B-model frames being provided to image buffer 250 and/or display system 260.

Grayscale and/or color processing may be self-adaptively adjusted based on user input (e.g., selections from the user input device 230), such as for enhancing the grayscale and/or color of a particular region.

The embodiments of the present application further provide a computer-readable program, wherein the program, when executed, causes a computer to perform, in a medical imaging system, the medical imaging method described in any of the foregoing embodiments.

The embodiments of the present application further provide a storage medium having a computer-readable program stored therein, wherein the computer-readable program causes a computer to perform, in a medical imaging system, the medical imaging method described in any of the foregoing embodiments.

A non-transitory computer-readable medium has a computer program stored therein, wherein the computer program has at least one code segment, and the at least one code segment is executable by a machine to cause the machine to perform the medical imaging method described in any of the foregoing embodiments.

The above embodiments merely provide illustrative descriptions of the embodiments of the present application. However, the present application is not limited thereto, and appropriate variations may be made on the basis of the above embodiments. For example, each of the above embodiments may be used independently, or one or more among the above embodiments may be combined.

The present application is described above with reference to specific embodiments. However, it should be clear to those skilled in the art that the foregoing description is merely illustrative and is not intended to limit the scope of protection of the present application. Various variations and modifications may be made by those skilled in the art according to the spirit and principle of the present application, and these variations and modifications also fall within the scope of the present application.

Preferred embodiments of the present application are described above with reference to the accompanying drawings. Many features and advantages of the implementations are clear according to the detailed description, and therefore the appended claims are intended to cover all these features and advantages that fall within the true spirit and scope of these implementations. In addition, as many modifications and changes could be easily conceived of by those skilled in the art, the embodiments of the present application are not limited to the illustrated and described precise structures and operations, but can encompass all appropriate modifications, changes, and equivalents that fall within the scope of the implementations.

The invention claimed is:

1. A medical imaging system, comprising:
- at least two medical imaging devices configured to image a subject;
- a memory storing instructions; and
- at least one processor configured to execute the instructions to:
  - control the at least two medical imaging devices to perform communication with each other;
  - generate an imaging protocol for different sites to be imaged of the subject, the imaging protocol comprising an allocation of the different sites to be imaged in the at least two medical imaging devices;
  - send the imaging protocol to each of the at least two medical imaging devices;

- control operation of the at least two medical imaging devices based on the imaging protocol to simultaneously image the subject;
  - receive imaging progress information of at least one of the medical imaging devices; and
  - automatically update, based on the imaging progress information, the imaging protocol for each of the at least two medical imaging devices.

2. The medical imaging system according to claim 1, wherein the at least two medical imaging devices comprises a scanning device and a display device, the scanning device being configured to scan at least one site to be imaged of the subject to obtain imaging data comprising information of the at least one site to be imaged, and the display device being configured to receive and display a signal from the at least one processor.

3. The medical imaging system according to claim 2, wherein the at least two medical imaging devices comprises an ultrasound imaging device comprising at least one patch probe.

4. The medical imaging system according to claim 1, wherein the at least one processor is further configured to execute the instruction to:
- acquire operation information of the at least two medical imaging devices, the operation information comprising at least one of computing power information, health information, and power supply information; and
- control, based on the operation information, at least one of the at least two medical imaging devices to be a master device.

5. The medical imaging system according to claim 1, wherein
- the imaging protocol further comprises the imaging progress information and/or imaging result information.

6. The medical imaging system according to claim 5, wherein the at least one processor is further configured to execute the instruction to:
- control at least one of the at least two medical imaging devices to display or output the received imaging progress information and/or imaging result information.

7. The medical imaging system according to claim 1, wherein the communication comprises:
- controlling the at least two medical imaging devices to perform communication with each other based on a predetermined communication protocol; or,
- selecting a communication protocol from among at least two communication protocols for the at least two medical imaging devices to perform communication with each other.

8. A medical imaging method, characterized by comprising:
- controlling at least two medical imaging devices to perform communication with each other;
- generating an imaging protocol for different sites to be imaged of a same subject to be imaged, the imaging protocol comprising an allocation of the different sites to be imaged in the at least two medical imaging devices;
- sending the imaging protocol to each of the at least two medical imaging devices;
- controlling operation of the at least two medical imaging devices based on the imaging protocol to simultaneously image the subject;
- receiving imaging progress information of at least one of the medical imaging devices; and automatically updating, based on the imaging progress information, the imaging protocol for each of the at least two medical imaging devices.

9. The medical imaging method according to claim 8, further comprising:

acquiring operation information of the at least two medical imaging devices, the operation information comprising at least one of computing power information, health information, and power supply information; and controlling, based on the operation information, at least one of the at least two medical imaging devices to be a master device.

10. The medical imaging method according to claim 8, wherein the imaging protocol further comprises the imaging progress information and/or imaging result information.

11. The medical imaging method according to claim 10, further comprising:

controlling at least one of the medical imaging devices to display or output the received imaging progress information and/or imaging result information.

12. The medical imaging method according to claim 8, wherein the communication comprises:

controlling the at least two medical imaging devices to perform communication with each other based on a predetermined communication protocol; or, selecting a communication protocol from among at least two communication protocols for the at least two medical imaging devices to perform communication with each other.

13. A non-transitory computer-readable medium, having a computer program stored therein, wherein the computer program has at least one code segment, and the at least one code segment is executable by a machine to cause the machine to:

control at least two medical imaging devices to perform communication with each other;

generate an imaging protocol for different sites to be imaged of the subject, the imaging protocol comprising an allocation of the different sites to be imaged in the at least two medical imaging devices;

send the imaging protocol to each of the at least two medical imaging devices;

control operation of the at least two medical imaging devices based on the imaging protocol to simultaneously image the subject;

receive imaging progress information of at least one of the medical imaging devices; and automatically update, based on the imaging progress information, the imaging protocol for each of the at least two medical imaging devices.

* * * * *